United States Patent
Tyortyalian

[11] Patent Number: 5,527,548
[45] Date of Patent: Jun. 18, 1996

[54] FOOD PRODUCTS CONTAINING BENZIMIDAZOLE

[76] Inventor: Carlos Tyortyalian, c/o Manoukian, 19 Avenue de l'Espérance, 91440 Bures sur Yvette, France

[21] Appl. No.: 367,190

[22] PCT Filed: Jul. 13, 1993

[86] PCT No.: PCT/FR93/00716

§ 371 Date: Jan. 13, 1995

§ 102(e) Date: Jan. 13, 1995

[87] PCT Pub. No.: WO94/02035

PCT Pub. Date: Feb. 3, 1994

[30] Foreign Application Priority Data

Jul. 15, 1992 [FR] France .................. 92 08743

[51] Int. Cl.$^6$ .......... A23L 1/30; A61K 31/415
[52] U.S. Cl. .......... 426/72; 426/648; 514/394; 514/396; 514/819; 514/926; 514/927
[58] Field of Search .................. 514/394, 396, 514/819, 926, 927; 426/72, 648

[56] References Cited

U.S. PATENT DOCUMENTS 4,056,108  11/1977  Schumacher et al. .................. 131/208

FOREIGN PATENT DOCUMENTS 1473823  3/1967  France .
2260995  2/1974  France .................. A61K 27/00

OTHER PUBLICATIONS

Food Science & Technology Abstracts, 1985. AC–No. 85–06–C0023. pp. 760–763.

Primary Examiner—John W. Rollins
Attorney, Agent, or Firm—Dennison, Meserole, Pollack & Scheiner

[57] ABSTRACT

A method for promoting digestibility of a food product having an acid character which, when ingested, causes stimulation and hypersecretion of gastric and/or duodenum mucosae. The method comprises incorporating into the food product a sufficient amount of benzimidazole or a benzimidazole compound of the formula:

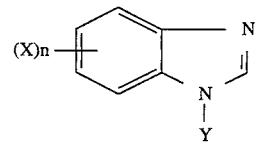

where X and Y independently represent an alkyl group, a phenyl group or a halogen atom and n=1 to 4.

11 Claims, No Drawings

FOOD PRODUCTS CONTAINING BENZIMIDAZOLE

BACKGROUND OF THE INVENTION

The present invention relates to food products and to methods for preparing and treating them. Said food products contain a chemical substance which makes them easier for the body to assimilate.

More precisely, the invention provides a solution to the problem of the assimilation of foods of acid nature which are known to stimulation gastric and duodenum secretions.

The assimilation of those food products often cause in healthy individuals, disorders of a benign nature (indigestion, stomach burns . . . ). In can, in other individuals, create, with time, more serious disorders, which could lead to ulcers or peritonitis.

The conventional treatments for that kind of ailments, consist in removing from the diet any food which stimulates gastric and duodenum secretions and/or in administering:

medicines intended for neutralizing gastric acidity, such as bicarbonate of soda; and/or
  medicines intended for reducing hypersecretion, such as atromine and belladona.

These latter medicines have disturbing secondary effects, just like the histamine and parathyroidal extract often used for reducing pains.

These conventional treatments are restraining and often involve expensive medicines, which are difficult to administer, and can even be dangerous on a long term basis.

SUMMARY OF THE INVENTION

It is therefore the object of the present invention to substitute to all or part only of said medicines, a product which is inexpensive, innocuous and of easy administration.

The present invention proposes to this effect to use benzimidazole and/or at least one of its derivatives, directly mixed with the food products.

Said benzimidazole has the following formula:

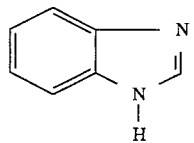

Its derivatives, whether by addition or substitution, advantageously have the following formula:

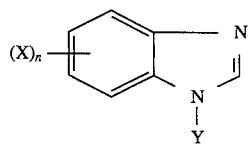

in which

X and Y are, independently, an alkyl group, notably methyl, a phenyl group, a halogen . . .

n is 1 to 4.

DETAILED DESCRIPTION OF THE INVENTION

Benzimidazole is wellknown as a chemical compound, its first synthesis going back to over a hundred years (synthesis by reaction of o-phenylenediamine with formic acid: Wundt, Ber. 11, 826 (1878)).

This compound is very stable, particularly under heat, and it can withstand the action of concentrated acids, such as sulfuric and hydrochloric acids, and of alkalis.

Moreover, this compound has a wellknown biological activity, due to its chemical relation with histamine, and to its presence in the molecule of vitamin B12 (where it forms a bridge between the cobalt and one of the lateral chains, bonding of said chain being achieved with an amino-alcohol residue).

Benzimidazole and its derivatives are also already known to have pharmacological properties, which are not incompatible with their use within the scope of the present invention.

For example, the action of some of its derivatives on vasomotricity has been described, as well as the action of others against malaria.

It has also been shown that some of its derivatives exhibited remarkable fungicidal properties, of spectrum higher than that of griseofulvine, which are due to the blocking of the protein synthesis but which can be inhibited by the antagonist action of adenine, guanine, nucleic acids and vitamin B12 . . .

A study of the various pharmacological properties of the benzimidazole and of its derivatives has revealed the innocuousness of those substances. In particular, the $LD_{50}$ of benzimidazole has been determined by the "Up and Down" method in mice. Said $LD_{50}$ varies after 30 days, from 0.520 to 0.610 mg/g.

In the course of his works, the Applicant has determined the selective affinity and persistant concentration of benzimidazole and its derivatives, at the level of the gastro-duodenum mucosae, as well as the advantage that there is in ingesting said product or products at the same time as food products liable to cause stimulation and hypersecretion of said mucosae.

The selective affinity of benzimidazole towards the gastric mucose in mice and dogs as well as in humans, was established by autoradiographic and gammagraphic techniques, using the benzimidazole labeled with carbon 14 or iodine 131 and injected by intraperitoneol or intraveinous route.

It was found in both cases that the distribution of the labeled product was homogeneous already 15 minutes after the injection, but that after 3 hours, the radioactivity of most of the tissues was very low, except for that of the stomach and of the gastric contents which continue to increase and keeps up for over 6 hours to disappear within 24 hours.

Said tests have also shown that the benzimidazole is easily and totally eliminated, especially through the urinary system, and is free of any residual toxicity both in animals and humans, even at the concentrations observed at the level of the gastro-duodenum mucosae.

The Applicant also measured the $ED_{50}$ in mice (22–28 g), in anti-salivation tests (salivation induced by subcutaneous injection of pilocarpine: $ED_{50}>100$ mg/kg p.o.) and intestinal motricity tests (using charcoal: $ED_{50}>100$ mg/kg p.o.).

Up to doses of over 100 mg/kg p.o., the benzimidazole has no effect on salivation and does not reduce intestinal motricity.

The present invention recommends the use of this compound and/or of at least one of its derivatives in food products.

It is therefore the object of the present invention to provide food products which contain benzimidazole and/or at least one of its derivatives, and more particularly food products the ingestion of which is known to cause the stimulation and hypersecretion of the gastric and/or duodenum mucosae; said food products being known for their acidity.

According to the invention, said food products contain said benzimidazole and/or at least one of its derivatives, in efficient quantity to arrive at the expected result which is to improve assimilation by the body system.

A perfect digestion of the products is thus reached in that said products have been made digestible.

The combination of the food product with the benzimidazole, and/or at least one of its derivatives, according to the invention, is very advantageous. It makes it possible to abort any gastro-duodenum non-tumorous disorders, to prevent pains (stomach pains) from occurring, after the ingestion of products known to be difficult to digest. It has a preventive action.

The Applicant has further established that gastric disorders also affected young children and newborn babies. Thus, according to one of its aspects, the invention relates to food products for children and/or newborn babies, which contain benzimidazole and/or at least one of its derivatives. One example is milk for newborn babies, in powder form if appropriate.

Examples of food products, which advantageously contain benzimidazole and/or one of its derivatives, according to the invention, are as follows: pasta, bread, sauces, jam, marmalade, jellies, sweets, ice-creams, chocolates, desserts, biscuits, coffee, tea, sausages, oils, . . .

Obviously, this list is not exhaustive.

It will be noted at this stage that, in the present text, the terms "food product" includes drinks such as alcoholic drinks, fruit juices, gaseous or non-gaseous mineral waters, . . .

The quantity of benzimidazole and/or analogue or analogues used is not critical insofar as the product is not toxic and has no secondary effects. An adult can ingest between 15 and 30 mg daily, against 5 to 15 mg for a newborn baby or a child (8–10 years old) without any danger.

It is of course advised to use a sufficient quantity of the product in order to obtain the expected result. Incidently, it should be noted that the presence of the benzimidazole, and/or of at least one of its derivatives, in the food products, does not affect either their flavor, (taste and smell), or their appearance.

The invention relates in particularly to:

bread containing, for 100 g, between 15 and 25 mg of benzimidazole and/or at least one of its derivatives;

coffee containing, for 1 kg, about 500 mg of benzimidazole and/or of at least one of its derivatives;

pasta containing, for 1 kg, about 150 mg of benzimidazole and/or of at least one of its derivatives;

sauces containing, for 100 g, between 50 and 60 mg of benzimidazole and/or of at least one of its derivatives;

jam containing, for 1 kg, about 100 mg of benzimidazole and/or of at least one of its derivatives;

alcoholized drinks such as whisky, cognac, liqueurs, wines, champagnes, . . . containing for example between 60 and 200 mg/liter of benzimidazole and/or of at least one of its derivatives;

beers containing for example between 30 and 70 mg/liter of benzimidazole and/or of at least one of its derivatives;

fruit juices or analogues, such as grape juice, orange juice, grapefruit juice, lemon juice, pineapple juice, peach juice, apple juice or lemonade, coca-cola or cider, . . . containing for example between 25 and 60 mg/liter of benzimidazole and/or of at least one of its derivatives;

gaseous or non-gaseous mineral water, . . . containing for example between 10 and 25 mg/liter of benzimidazole and/or of at least one of its derivatives.

For making the bread which, according to the invention, contains benzimidazole and/or at least one of its derivatives, the flour used will advantageously contain between 20 and 25 mg of said benzimidazole and/or of at least one of its derivatives per kg.

It is clear from the foregoing that the action of the benzimidazole and/or of at least one of its derivatives, is not strictly limited to such or such a quantity for such or such a type of product.

The combination of a food product with benzimidazole, and/or at least one of its derivatives, does not either raise any elaboration problems, particularly due to the stability of said chemical substances.

According to another of its aspects, the invention relates to a method for preparing a food product and to a method for treating a food product so as to facilitate its assimilation by the body system, said methods consisting in:

either including benzimidazole and/or at least one of its derivatives, during the preparation of the food product; or adding said benzimidazole and/or at least one of its derivatives in said prepared food product.

The use of said benzimidazole and/or at least one of its derivatives during the preparation of the product and at the final product stage, cannot be excluded.

The invention therefore proposes a novel use of the benzimidazole and of its derivatives, in food products, in order to make them easier to assimilate for the body system. In other words, the invention proposes a method to facilitate the assimilation of food products in the body system, which method consists in incorporating benzimidazole and/or at least one of its derivatives therein.

What is claimed is:

1. A method for promoting digestibility of a food product having an acid character which, when ingested, causes stimulation and hypersecretion of gastric and/or duodenum mucosae, comprising incorporating into the food product an amount sufficient to promote said digestibility of a benzimidazole component selected form the group consisting of benzimidazole and a benzimidazole compound of the chemical formula:

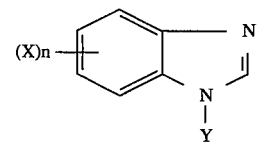

wherein:

X and Y independently represent an alkyl group, a phenyl group or a halogen atom; and n=1 to 4.

2. The method of claim 1, wherein said food product is selected from the group consisting of a food product for children and a food product for newborn babies.

3. The method of claim 1, wherein said food product is milk for newborn babies.

4. The method of claim 3, wherein said milk is in powder form.

5. The method of claim 1, wherein said food product is selected from the group consisting of pasta, bread, sauces, jam, marmalade, jellies, sweets, ice cream, chocolate, desserts, biscuits, coffee, tea, sausages, oils, a beverage, an alcoholic beverage, fruit juices, gaseous mineral water, non-gaseous mineral water and beer.

6. The method of claim 1, wherein said food product is bread and contains, per 100 grams, from 15 to 25 mg of said benzimidazole component.

7. The method of claim 1, wherein said food product is coffee and contains, per 1 kilogram, about 500 mg of said benzimidazole component.

8. The method of claim 1, wherein the food product is pasta and contains per kilogram, about 150 mg of said benzimidazole component.

9. The method of claim 1, wherein said food product is a sauce and contains, per 100 grams, from 50 to 60 mg of said benzimidazole component.

10. The method of claim 1, wherein said food product is a jam and contains, per kilogram, about 100 mg of said benzimidazole component.

11. The method of claim 1, wherein the alkyl group is a methyl group.

* * * * *